(12) United States Patent
Sun et al.

(10) Patent No.: US 8,921,416 B2
(45) Date of Patent: Dec. 30, 2014

(54) DRONEDARONE SOLID DISPERSION AND PREPARATION METHOD THEREOF

(75) Inventors: Piaoyang Sun, Jiangsu (CN); Kai Pan, Jiangsu (CN); Yuxia Wu, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 9 days.

(21) Appl. No.: 13/812,175

(22) PCT Filed: May 31, 2011

(86) PCT No.: PCT/CN2011/074989
§ 371 (c)(1),
(2), (4) Date: Jan. 25, 2013

(87) PCT Pub. No.: WO2012/013088
PCT Pub. Date: Feb. 2, 2012

(65) Prior Publication Data
US 2013/0123353 A1    May 16, 2013

(30) Foreign Application Priority Data
Jul. 30, 2010   (CN) .......................... 2010 1 0251305

(51) Int. Cl.
*A61K 31/343* (2006.01)
*A61K 9/14* (2006.01)

(52) U.S. Cl.
CPC ............... *A61K 31/343* (2013.01); *A61K 9/146* (2013.01)
USPC .......................................... 514/469

(58) Field of Classification Search
CPC ............................. A61K 31/343; A61K 9/146
USPC .......................................... 514/469
See application file for complete search history.

(56) References Cited

U.S. PATENT DOCUMENTS

| 2004/0044070 | A1 | 3/2004 | Bourriague-Seve et al. |
| 2007/0243257 | A1* | 10/2007 | Bedos et al. ................. 424/486 |

FOREIGN PATENT DOCUMENTS

| CN | 1091593 C | 10/2002 |
| CN | 1608622 A | 4/2005 |
| CN | 101032464 A | 9/2007 |
| CN | 101039657 A | 9/2007 |
| CN | 101081213 A | 12/2007 |
| CN | 101152154 A | 4/2008 |

OTHER PUBLICATIONS

Folttmann et al. (Drug Delivery Technology, Jun. 2008, vol. 8, No. 6).*
Int'l Search Report issued on Sep. 8, 2011 in Int'l Application No. PCT/CN2011/074989.

* cited by examiner

*Primary Examiner* — Janet Epps-Smith
*Assistant Examiner* — Courtney Brown
(74) *Attorney, Agent, or Firm* — Panitch Schwarze Belisario & Nadel LLP (57) ABSTRACT

A dronedarone solid dispersion and preparation method thereof are disclosed. The solid dispersion is composed of active ingredient dronedarone or its pharmaceutically acceptable salt and a carrier material, wherein the carrier material is povidone, copovidone, hydroxypropyl cellulose, or a mixture thereof.

18 Claims, 7 Drawing Sheets

Report of the X-ray diffraction test

Filename: y-dronedarone raw drug
Sample name: dronedarone raw drug
Number of repetition: 1
Initiative angle: 3          Terminational angle: 40    Step: .02
Scan    speed: 10            Integration time: .1        Target: Cu
Pipe flow/pipe pressure: 40kV50mA   Slit: 1, 1, 0.3, 0.6
Filter: Graphite             Testing time: #2009-12-01 15: 17: 50#

| No. | 2θ | d value | count | relative intensity | half-height | integration intensity |
|---|---|---|---|---|---|---|
| 1 | 7.640 | 11.562 | 3310 | 85 | 0.280 | 49325 |
| 2 | 8.060 | 10.960 | 2734 | 70 | 0.240 | 34919 |
| 3 | 11.860 | 7.456 | 726 | 18 | 0.280 | 10814 |
| 4 | 12.980 | 6.815 | 1495 | 38 | 0.280 | 22284 |
| 5 | 13.800 | 6.412 | 3876 | 100 | 0.200 | 41263 |
| 6 | 14.240 | 6.215 | 613 | 15 | 0.240 | 7833 |
| 7 | 15.260 | 5.801 | 1112 | 28 | 0.280 | 16575 |
| 8 | 15.680 | 5.647 | 2116 | 54 | 0.280 | 22519 |
| 9 | 16.200 | 5.467 | 1516 | 39 | 0.280 | 22589 |
| 10 | 18.780 | 4.721 | 661 | 17 | 0.320 | 11250 |
| 11 | 19.940 | 4.449 | 1582 | 40 | 0.240 | 20206 |
| 12 | 20.360 | 4.358 | 669 | 17 | 0.240 | 8541 |
| 13 | 20.720 | 4.283 | 806 | 20 | 0.240 | 10291 |
| 14 | 21.400 | 4.149 | 3230 | 83 | 0.320 | 55010 |
| 15 | 21.600 | 4.111 | 2875 | 74 | 0.800 | 122409 |
| 16 | 22.620 | 3.928 | 650 | 16 | 0.280 | 9683 |
| 17 | 23.880 | 3.723 | 1161 | 29 | 0.280 | 17296 |
| 18 | 24.320 | 3.657 | 1054 | 27 | 0.200 | 11219 |
| 19 | 24.960 | 3.564 | 551 | 14 | 0.360 | 10552 |
| 20 | 26.060 | 3.416 | 2121 | 54 | 0.320 | 36130 |
| 21 | 26.860 | 3.316 | 630 | 16 | 0.320 | 10726 |
| 22 | 27.620 | 3.227 | 700 | 18 | 0.600 | 22345 |
| 23 | 32.740 | 2.733 | 452 | 11 | 0.280 | 6731 |

DRONEDARONE SOLID DISPERSION AND PREPARATION METHOD THEREOF

CROSS-REFERENCE TO RELATED APPLICATIONS

This application is a Section 371 of International Application No. PCT/CN2011/074989, filed on May 31, 2011, which was published in the Chinese language on Feb. 2, 2012, under International Publication No. WO 2012/013088 A1, and the disclosure of which is incorporated herein by reference.

FIELD OF THE INVENTION

The invention relates to a solid dispersion comprising dronedarone, or a pharmaceutically acceptable salt thereof, and a preparation method thereof.

BACKGROUND OF THE INVENTION

The chemical name of dronedarone is N-(2-Butyl-3-(4-(3-(dibutylamino)propoxy) benzoyl)-5-benzofuranyl)methanesulfonamide, the molecular formula is $C_{31}H_{44}N_2O_5S$ and the molecular weight is 556.765 Dalton.

Dronedarone is a new antiarrhythmic drug developed by Sanofi-Aventis and is approved on Jul. 1, 2009 by the U.S. FDA.

The solubility of dronedarone in an aqueous solution is pH-dependent. The solubility of dronedarone at pH 3 to 5 is maximal (about 1 to 2 mg/ml), but its solubility at pH 6 to 7 is remarkably decreased (about 10 µg/ml at pH=7). The physiological pH from the stomach to the gut of a human body gradually increases, thus even if the drug is dissolved in the stomach after administration, the drug may still precipitate out after it enters the intestine through gastric emptying due to the increased pH. The drug cannot be kept in the intestinal juice in a molecular form and cannot achieve a transmembrane absorption due to the large amount of precipitation of it. This affects the absorption of the drug and leads to a low bioavailability. Thus, it is important to increase the dissolution rate of the drug so as to improve the bioavailability and clinical therapeutic effect. The solubility of the drug shall be increased with pharmaceutical technology to avoid its precipitation in a neutral medium, thereby improving the bioavailability of the drug.

In order to improve the solubility and the bioavailability of the said drug, a dronedarone hydrochloride injection is disclosed in an US patent application (US20040044070A1), according to which a β-cyclodextrin derivative is added into a buffer system (pH=3-5) to improve the solubility of the active ingredients. However, the method disclosed in that application has several disadvantages such as complex manufacturing process, low drug loading and poor stability. A solid pharmaceutical composition comprising benzofuran derivative is disclosed in a Chinese patent (ZL98808158.X), according to which the dronedarone hydrochloride will not precipitate out in a large amount after it is diluted in a high pH solution and then kept in a solution at pH 6-7 via the use of a non-ionotropic surfactant, especially poloxamer class of non-ionotropic surfactants. This improves the bioavailability of the drug under fasting conditions. However, surfactants used in that method will inevitably bring about a certain stimulatory effect and toxicity on human bodies. A capsule or tablet comprising a micronized dronedarone, surfactants and a hydrophilic polymer serving as a hydrotropy agent is disclosed in a Chinese patent application (CN 200610113479.5), according to which the cumulative dissolution rate of the capsule or tablet is greatly increased in a PBS at pH6.7. However, the method disclosed in this Chinese patent application also has several disadvantages such as a complex preparation process, high energy consumption, low drug loading, and dosage forms which are not suitable for the clinical application. Furthermore, anionic surfactants are used in that method, which have a certain stimulatory effect and toxicity on human bodies.

Currently, micronized technology, inclusion technique and solid dispersion technology are main methods to improve the solubility and dissolution rate of poorly soluble drugs. Existing studies show that, after being micronized, the particle sizes of a drug are reduced, the surface area and dissolution rate are increased. However when the particle sizes are reduced to a certain extent, the free energy of the microparticles is increased dramatically. The particles will spontaneously aggregate during storage, or after entering the body, resulting in reduced dissolution rate. Due to the restriction caused by the molecular weight and space structure of the drugs, the inclusion technology only has a low success rate. Even though an inclusion complex can be formed, there are still many problems such as low drug loading and the like.

A solid dispersion (SD) is a dispersion system present in a solid form formed by highly dispersing a drug into a solid carrier. The drug is present in the carrier in a form of molecular state, colloidal state, metastable state, microcrystalline state, and amorphous state, etc. The solubility and dissolution rate of the drug present in an amorphous state (high energy state) are larger than those of the drug present in other crystalline states.

There are relatively more researches in solid dispersion technique for improving the solubility and dissolution rate of poorly soluble drugs and more significant effects have been obtained. However there are also problems along with this technique, such as a complex process, a low drug loading and the like. Especially a large amount of carrier is required in order to achieve significant effects, which results in low drug loading and limited clinical use. For example, a pharmaceutical composition comprising a solid dispersion with the polymer matrix is disclosed in a Chinese patent application (CN101039657A), of which a solid dispersion is prepared with a hot melting extrusion method by using polydextrose and another polymer as a carrier. In order to achieve a desirable result, the method in that invention needs two carriers including polydextrose for the preparation of the solid dispersion, and the drug loading of which is low.

Therefore, there is a need to provide a solid dispersion of dronedarone or salts thereof, of which not only the solubility or dissolution rate is improved, but also a higher drug loading is achieved.

SUMMARY OF THE INVENTION

In one aspect of the present invention, after comparing and screening different materials, a solid dispersion comprising dronedarone or a salt thereof and a specific polymer carrier is prepared, thereby achieving improved solubility or dissolution rate of dronedarone and increased drug loading of the solid dispersion simultaneously by only using one polymer carrier without the use of a surfactant.

In another aspect, the dronedarone in a solid dispersion prepared by a solvent method of the present invention is present in an amorphous state, which has greatly improved drug solubility. In addition, after removing the organic solvent through drying under reduced pressure, the resulting solid dispersion has good micromeritic properties, better fluidity and compressibility than those of the solid dispersion prepared with methods of prior art.

Specifically, the present invention provides an amorphous dronedarone solid dispersion, wherein said solid dispersion is composed of dronaderone or a pharmaceutically acceptable salt thereof serving as an active ingredient, and a carrier material.

In the solid dispersion of the present invention, said carrier is selected from the group consisting of hydrophilic polymeric carriers such as povidone, copovidone, hydroxypropyl cellulose and the like, wherein povidone and copovidone are preferred.

Said povidone is selected from such as povidone K-17, povidone K-25, povidone K-30, povidone K-90 and the like; said copovidone (polyvinyl pyrrolidone-vinyl acetate vinyl acetate copolymer) is selected from such as copovidones of which the brand names are Plasdone®S-630 or Kollidon®VA64 and the like; said hydroxypropyl cellulose is selected from the hydroxypropyl celluloses of which the brand names are Klucel® HXF, Klucel® HF, Klucel® MF, Klucel® GF, Klucel® JF, Klucel® LF, Klucel® EF, Klucel® EXF and the like.

The inventors of the present invention surprisingly discovered by screening the hydrophilic carriers that solid dispersions of dronedarone containing the hydrophilic carriers described above show a higher solubility and drug loading than those of the prior art (solid dispersions of dronedarone containing polydextrose and another matrix, or pharmaceutical compositions containing non-ionic surfactant). The compressibility and fluidity of the solid dispersion powder prepared with the above hydrophilic carriers are also better than those in the prior art. The said solid dispersion powder is easy to be further prepared into oral formulations such as tablets, capsules and the like.

In the present invention, the weight ratio of dronedarone used as the active pharmaceutical ingredient to the carrier material is 1:0.2-15, preferably 1:0.5-10, more preferably 1:1.0-7.5, most preferably 1:1.5-5.0. The salt of dronedarone in the solid dispersion of the present invention is selected from the group consisting of hydrochloride, citrate, maleate and tartrate salts, wherein the hydrochloride salt is preferred.

In another aspect of the present invention, a preparation method of said solid dispersion is provided. The solid dispersion is prepared with a solvent method or a hot melting extrusion method. It is preferable to use the solvent method (also called a co-precipitation method) to prepare the solid dispersion of the present invention.

The solid dispersion of the present invention can be prepared with the following method comprising the following steps:
(1) dissolving the active ingredient and the polymeric carrier material in a solvent; and
(2) removing the solvent.

In step (1), it is preferable to use an organic solvent which is selected from the group consisting of dichloromethane, methanol, ethanol, isopropanol, acetone, acetonitrile, chloroform and any suitable organic solvents. Preferably, the organic solvent is selected from the group consisting of dichloromethane, methanol and ethanol. In step (2), the solvent can be removed through drying under reduced pressure, spray drying or freeze-drying method, wherein drying under reduced pressure method is preferred.

Said organic solvent is one or a mixture of several selected from the group consisting of dichloromethane, methanol, ethanol, acetone, chloroform, and isopropanol; the weight ratio of the total weight of dronedarone and the carrier to the organic solvent is 1:1.0-10.0, preferably 1:1.0-5.0.

As to the solid dispersion drying process, drying under reduced pressure and spray drying are the most widely used method currently. And the products prepared with spray drying usually have better solubility, which makes it be used more widely. However, it is surprisingly found by the inventors through studies that the solubilities of the solid dispersions prepared with these two drying methods have no significant differences, while the micromeritic properties (compressibility and fluidity) of the solid dispersions prepared with drying under reduced pressure are apparently better than those of the solid dispersions prepared with spray drying method.

In the present invention, not any endothermic peaks are shown in the DSC scan spectrum of the amorphous dronedarone and not any crystalline diffraction peaks are shown in its powder X-ray diffraction spectrum, indicating that dronedarone in the solid dispersion of present invention is present in an amorphous state.

Compared with the prior art, the present invention has the following advantages:

1. The solid dispersion of present invention does not comprise any surfactants such that the stimulatory effect and toxicity of the surfactant on the human body as that of the prior art (e.g. Chinese patent ZL98808158.X and Chinese patent application CN 200610113479.5) can be avoided.
2. The solubility of a solid dispersion of the present invention in a medium at pH 6.8 is higher than those of the prior art (including the dronedarone solid dispersion comprising polydextrose and another matrix (CN101039657A), or the pharmaceutical composition comprising a non-ionic surfactant (ZL98808158.X)), wherein the solid dispersion according to the present invention comprises dronedarone hydrochloride as an active ingredient and a high hydrophilic polymer material as a carrier.
3. The solid dispersion prepared in the present invention has an increased drug loading while maintaining a higher solubility or dissolution rate. Furthermore, its powder compressibility and fluidity are also better.

BRIEF DESCRIPTION OF THE DRAWINGS

From the following accompanying drawings, the above and other objects and features of the present invention will become apparent, which respectively show.

DETAILED DESCRIPTION OF THE INVENTION

1. The Effects of Different Carriers on the Solubility of Dronedarone Hydrochloride in the Solid Dispersion The weight ratio of the drug to the carrier was 1:5. Different hydrophilic polymeric carrier materials were selected from the group consisting of polyethylene glycol 6000, poloxamer 188, PVP K30, Klucel® EF, Plasdone® S-630, mannitol and combinations thereof respectively. 12 parts by weight of dichloromathane were added into the drug and carrier mixture, and was dissolved by stirring. Then the solution was transferred to a vacuum oven, maintained at 55° C., dried under reduced pressure for 48 h. Then the dry mass was crushed with a 100 mesh sieve, thereby the solid dispersion of dronedarone was obtained. The solubilities of the solid dispersion in the phosphate buffered saline (PBS) at pH6.8 were measured as follows.

TABLE 1

The effects of different hydrophilic carrier materials on the solubilities of dronedarone

| No. | Active Ingredient | carrier | 24 h solubility (µg/ml) |
|---|---|---|---|
| 1 | Dronedarone hydrochloride | None | 12.0 |
| 2 | Dronedarone hydrochloride | Polyethylene glycol (PEG) 6000 | 33.9 |
| 3 | Dronedarone hydrochloride | Poloxamer 188 | 39.1 |
| 4 | Dronedarone hydrochloride | PVP K30 | 161.5 |
| 5 | Dronedarone hydrochloride | Klucel ® EF | 155.7 |

TABLE 1-continued

The effects of different hydrophilic carrier materials on the solubilities of dronedarone

| No. | Active Ingredient | carrier | 24 h solubility (µg/ml) |
|---|---|---|---|
| 6 | Dronedarone hydrochloride | Plasdone ® S-630 | 150.2 |
| 7 | Dronedarone hydrochloride | mannitol | 27.0 |
| 8 | Dronedarone hydrochloride | PVP K30 & PEG 6000 (1:1) | 104.5 |
| 9 | Dronedarone hydrochloride | PVP K30 & Poloxamer 188 (1:1) | 110.2 |
| 10 | Dronedarone hydrochloride | Klucel ® EF & PEG 6000 (1:1) | 90.4 |
| 11 | Dronedarone hydrochloride | Klucel ® EF & Poloxamer 188 (1:1) | 94.8 |

Figure 1:
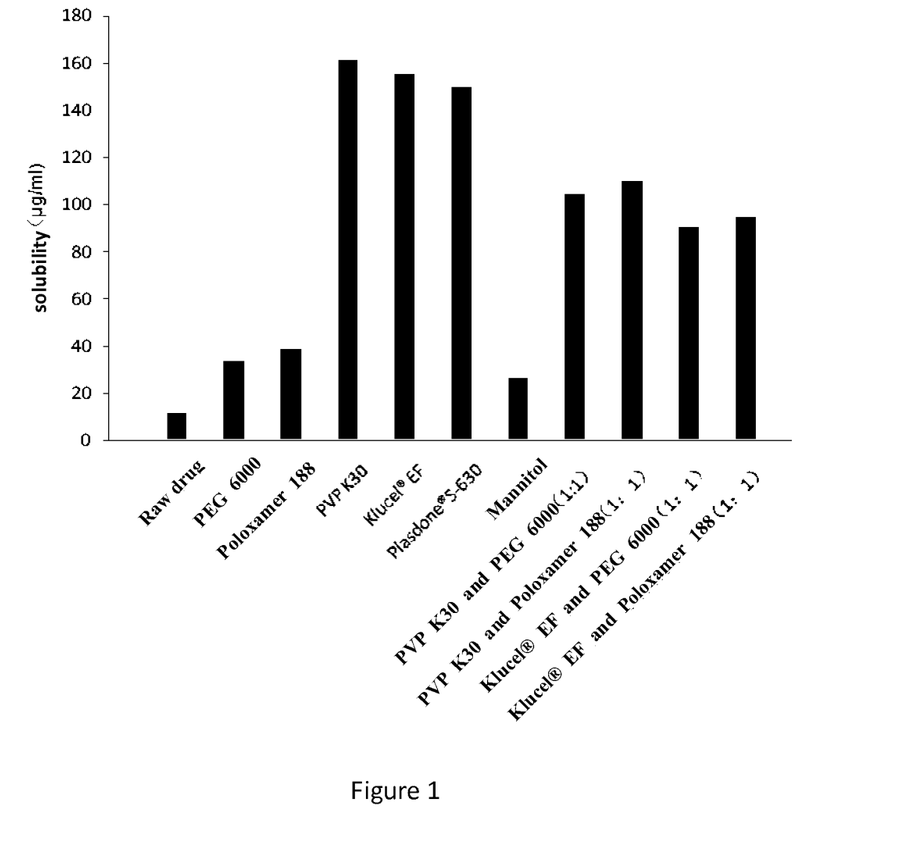
FIG. 1: the effects of different carriers on the solubility of dronedarone hydrochloride in the solid dispersion.

As showed in Table 1 and FIG. 1, when the mass ratio of drug to carrier was same, the solubilities of dronedarone in the solid dispersions prepared with povidone, copovidone and hydroxypropyl cellulose among the various hydrophilic carrier materials were significantly increased, and the addition of surfactant exhibited no significant influence on the solubilities of the solid dispersion of dronedarone. That is, good results can be achieved by using these materials alone, wherein Povidone K-30 exhibited the best effect, followed by hydroxypropyl cellulose (Klucel® EF) and copovidone (Plasdone® S-630).

2. The Effects of Different Amount and Different Type of Carriers on the Solubilities of Dronedarone Solid dispersions comprising dronedarone hydrochloride were prepared by using povidone, hydroxypropyl cellulose and copovidone as a carrier at different drug:carrier ratios according to the following method:

Two parts by weight of methylene chloride were added and then the mixture was dissolved by stirring. Then the solution was transferred to a vacuum oven, maintained at 55° C., dried under reduced pressure for 48 h. The dried mass was crushed with a 100 mesh sieve and thereby the solid dispersion of dronedarone hydrochloride was obtained.

24 h Solubility Determination: aliquots of the prepared solid dispersion were added into a 100 ml conical flask respectively. Then 50 ml PBS pH6.8 were added. The conical flask was sealed and placed in a thermostatic waterbath shaker and shaked at a set temperature of 37° C. for 24 h. After 24 hours, 10 mL of the solution were taken and filtrated. The initial 4 mL of the filtrate were abandoned and the subsequent filtrate were taken and diluted with PBS pH6.8 to a corresponding folds. The UV absorbance at 290 nm was measured with a UV spectrophotometer. Then the drug solubilities were calculated. The 24 h solubility of crystalline dronedarone hydrochloride was 12.0 µg/ml.

TABLE 2 the effects of different carriers and different drug: carrier weight ratios on the 24 h solubilities of the solid dispersions

| Hydrophilic carriers | 24 h solubility (µg/ml) API:carrier | | | | | | | | |
|---|---|---|---|---|---|---|---|---|---|
| / | 1:0.5 | 1:1 | 1:1.5 | 1:2 | 1:2.5 | 1:3 | 1:5 | 1:7.5 | 1:10 |
| PVP K30 | 63.5 | 119.2 | 155.2 | 157.5 | 160.4 | 163.2 | 161.5 | 123.8 | 75.4 |
| PVP-K17 | 62.1 | 110.7 | 135.6 | 141.5 | 151.3 | 160.8 | 157.6 | 109.6 | 86.2 |
| PVP-K25 | 59.2 | 107.4 | 142.3 | 151.8 | 153.4 | 159.3 | 156.4 | 114.5 | 81.9 |
| PVP-K90 | 59.6 | 96.8 | 129.4 | 138.6 | 149.8 | 151.2 | 150.4 | 87.3 | 70.5 |
| Klucel ® EF | 55.2 | 102.4 | 130.5 | 143.3 | 152.6 | 157.4 | 155.8 | 105.5 | 69.4 |
| Klucel ® LF | 60.1 | 105.9 | 136.4 | 144.1 | 146.9 | 155.1 | 152.6 | 96.7 | 67.5 |
| Plasdone ® S-630 | 62.0 | 96.8 | 135.7 | 141.5 | 145.6 | 152.3 | 150.8 | 85.9 | 63.8 |
| Polydextrose + copovidone (1:1) | 45.3 | 57.2 | 69.6 | 86.5 | 98.4 | 103.9 | 103.3 | 63.8 | 50.2 |

As shown in the results, the solubility of dronedarone hydrochloride in the solid dispersion of present invention in a medium at pH 6.8 not only was significantly increased compared with the crystalline dronedarone hydrochloride raw drug, but also was significantly increased compared with those of the dronedarone hydrochlorides in the solid dispersions prepared with polydextrose and copovidone (1:1) of various ratios. A good solubility can be achieved by the solid dispersion of dronedarone which used povidone, hydroxypropyl cellulose and copovidone as a hydrophilic polymeric carrier.

In addition, it was found that the solubilities of the solid dispersions prepared within the drug: carrier weight ratio from 1:1.0 to 1:7.5 were better, and those from 1:1.5 to 1:5 were the best.

3. The Comparison of Different Preparation Methods

Several methods were used to prepare the solid dispersions at the dronedarone hydrochloride:Povidone ratio of 1:1.5 (or 1:3).

Comparative Example 1

Hot Melting Extrusion Method 1 part by weight of dronedarone hydrochloride and 3.0 parts by weight of Povidone PVP K-30 were weighted and mixed for 10 min in a polyethylene bag, and placed into a feed hopper of the twin-screw hot melting extruder. The parameters of the twin-screw extruder were set as follows: Host Frequency: 3.5 Hz; feed frequency: 3.0 Hz; temperature of each district: 140° C. After the temperature of each district is stable, the machine was switched on and the liquid fluid flowed from the die was collected and cooled to be solid at room temperature and crushed with a 100 mesh sieve. Then the solid dispersion of dronedarone was obtained.

Comparative Example 2

Solvent Spray Drying Method 1 part by weight of dronedarone hydrochloride and 3.0 parts by weight of Povidone PVP K-30 were weighted, and then 12 parts by weight of dichloromethane were added, and stirred until the solution became clarified. The solution was spray dried and at the same time the inlet and outlet temperatures of the spray drier (Mini Spray Dryer, B290, Buchi, Switzerland) were maintained at 90° C. and 55° C. respectively. Then the sample was collect and the solid dispersion of dronedarone was obtained.

Comparative Example 3

Solvent Vacuum Drying Method 1 part by weight of dronedarone hydrochloride and 3.0 parts by weight of Povidone PVP K-30 were weighted and 12 parts by weight of dichloromethane were added into, and then stirred until the solution became clarified. The solution was transferred to a vacuum oven and maintained at 55° C., then dried under reduced pressure for 48 h and the dry mass was crushed with a 100 mesh sieve and thereby the solid dispersion of dronedarone was obtained.

Test Example 1

The Solubility of the Solid Dispersion

| sample | method | 24 h solubility (μg/ml) |
|---|---|---|
| powder of comparative example 1 | hot melting extrusion method | 155.7 |
| powder of comparative example 2 | solvent spray drying method | 158.2 |
| powder of comparative example 3 | solvent vacuum drying method | 163.2 |

Test Example 2

Micromeritic Properties of the Solid Dispersion Powder

| sample | bulk density (g/ml) | tap density (g/ml) | carr index (%) | angle of repose (°) |
|---|---|---|---|---|
| powder of comparative example 1 | 0.476 | 0.683 | 30.3 | 44.3 |
| powder of comparative example 2 | 0.306 | 0.502 | 39.0 | 63.4 |
| powder of comparative example 3 | 0.579 | 0.770 | 24.8 | 41.5 |

It was found that different preparation methods had no significant influences on the solubility of the drug at the same drug-carrier ratio and all of these solid dispersions had better solubilizing properties.

Carr index was used to evaluate the compressibility of the powder, and the angle of repose was used to evaluate the fluidity of the powder. A smaller Carr index indicated a better compressibility, and a smaller angle of repose indicated a better fluidity. As shown in the results, solubilities of solid dispersions prepared with solvent methods were better than those prepared with hot melting extrusion method. Furthermore, the micromeritic properties of the solid dispersions prepared with a drying under reduced pressure are better if a solvent method was used. The powder prepared with a drying under reduced pressure is easier to be prepared into oral solid preparations such as tablets or capsules.

4. EXAMPLES

The following examples were provided to further illustrate the present invention, but it is not to be construed as being limited thereto. Example: The preparation of the solid dispersion of Dronedarone hydrochloride (produced by JIANGSU HENGRUI MEDICINE CO., LTD).

Example 1

One part by weight of dronedarone hydrochloride and 0.5 parts by weight of PVP K-30 were weighted and three parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 2

One part by weight of dronedarone hydrochloride and 1.5 parts by weight of PVP K-30 were weighted and five parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 3

One part by weight of dronedarone hydrochloride and three parts by weight of PVP K-30 were weighted and twelve parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 4

One part by weight of dronedarone hydrochloride and five parts by weight of PVP K-30 were weighted and twelve parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 5

One part by weight of dronedarone hydrochloride and 1.5 parts by weight of PVP K-17 were weighted and twelve parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 6

One part by weight of dronedarone hydrochloride and 1.5 parts by weight of PVP K-30 were weighted and five parts by weight of methanol were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 7

One part by weight of dronedarone hydrochloride and 1.5 parts by weight of PVP K-30 were weighted and 12.5 parts by weight of anhydrous ethanol were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 8

One part by weight of dronedarone hydrochloride and 1.5 parts by weight of PVP K-25 were weighted and five parts by weight of methanol were added into and the mixture was dissolved by stirring. Then the solutions was transferred to a vacuum oven and dried under reduced pressure at 55° C. for 48 h. The dry mass was crushed and passed through a 100 mesh sieve thereby the solid dispersion of dronedarone hydrochloride was obtained.

Example 9

One part by weight of dronedarone hydrochloride and 1.5 parts by weight of PVP K-90 were weighted and five parts by weight of methanol were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 10

One part by weight of dronedarone hydrochloride and 1.5 parts by weight of Klucel® EF were weighted and five parts by weight of dichloromethane-anhydrous ethanol (4:1) were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 11

One part by weight of dronedarone hydrochloride and 1.5 parts by weight of Klucel® LF were weighted and 12.5 parts by weight of anhydrous ethanol were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 12

One part by weight of dronedarone hydrochloride and 2.5 parts by weight of Plasdone®S-630 were weighted and 12.5 parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 13

One part by weight of dronedarone hydrochloride and 0.2 parts by weight of PVP K-30 were weighted and 12.5 parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Example 14

One part by weight of dronedarone hydrochloride and 10 parts by weight of Plasdone®S-630 were weighted and 12.5 parts by weight of dichloromethane were added into and the mixture was dissolved by stirring. Then the solution was transferred to a vacuum oven and dried under reduced pressure at 55° C. for 48 h. The dry mass was crushed and passed through a 100 mesh sieve thereby the solid dispersion of dronedarone hydrochloride was obtained.

Test Example 1

Micromeritic Properties of the Solid Dispersion Powder

The micromeritic properties of the solid dispersion powder obtained in the Examples above were measured as follows:

| sample | bulk density (g/ml) | tap density (g/ml) | Carr index (%) | angle of repose (°) |
| --- | --- | --- | --- | --- |
| powder of Example 1 | 0.546 | 0.742 | 26.4 | 43.6 |
| powder of Example 3 | 0.579 | 0.770 | 24.8 | 41.5 |
| powder of Example 6 | 0.568 | 0.759 | 25.2 | 42.6 |
| powder of Example 8 | 0.564 | 0.758 | 25.6 | 42.5 |
| powder of Example 10 | 0.583 | 0.775 | 24.8 | 41.3 |
| powder of Example 12 | 0.591 | 0.783 | 24.5 | 42.2 |

As shown in the above table, if the drying under reduced pressure was used, good micromeritic properties can be obtained by all the prepared solid dispersions. The types of the carriers and the weight ratios of the carriers to the active ingredient had no significant effects on micromeritic properties of the solid dispersions.

Test Example 2

Differential Scanning Calorimetry Tests (DSC)

Working conditions: 10° C./min, temperature range: 50-300° C. The differential scanning calorimetry tests were conducted on the dronedarone hydrochloride raw material, povidone PVP-K30 and the solid dispersion prepared in Example 2.

Figure 2:
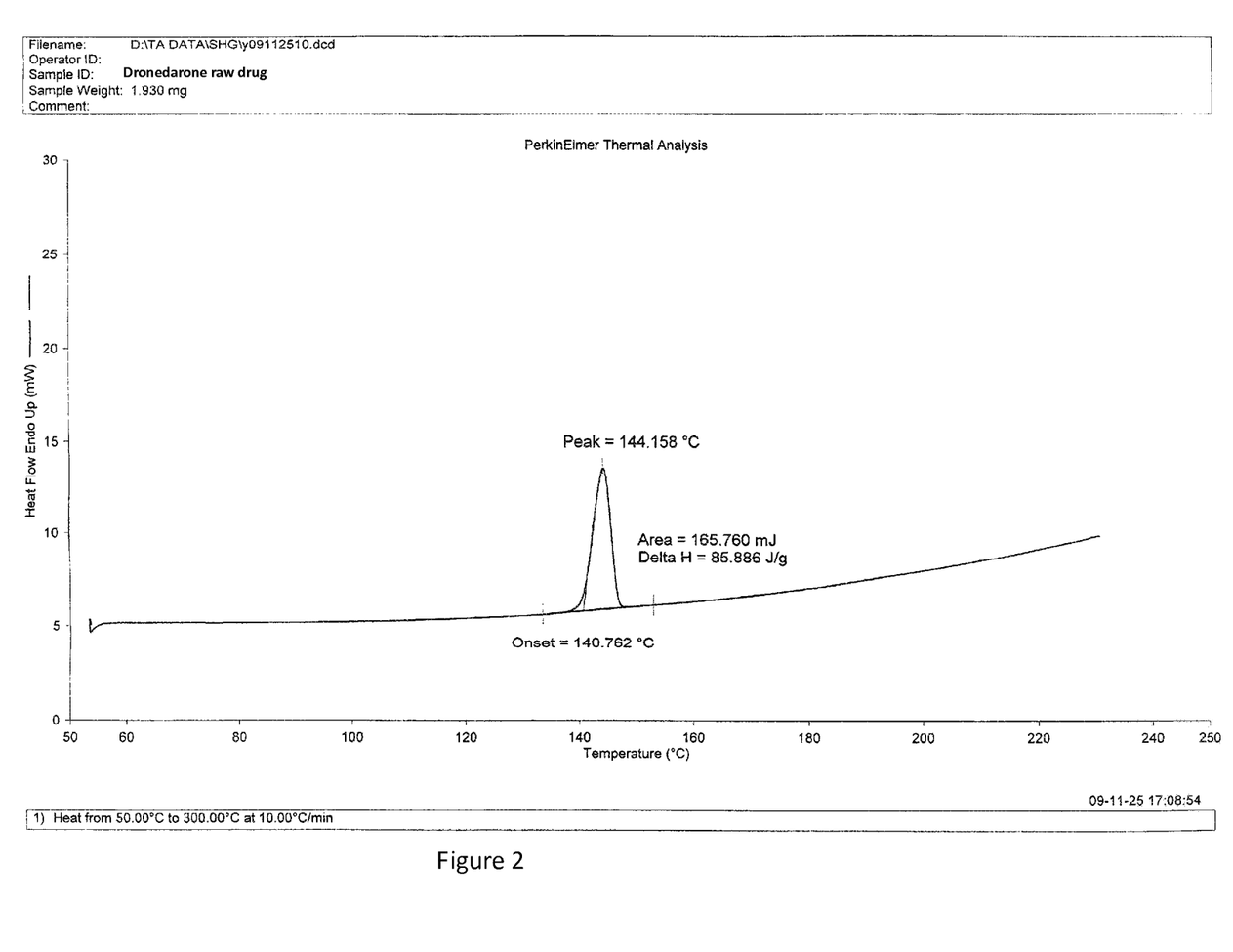
FIG. 2: the DSC spectrum of dronedarone hydrochloride.
Figure 3:
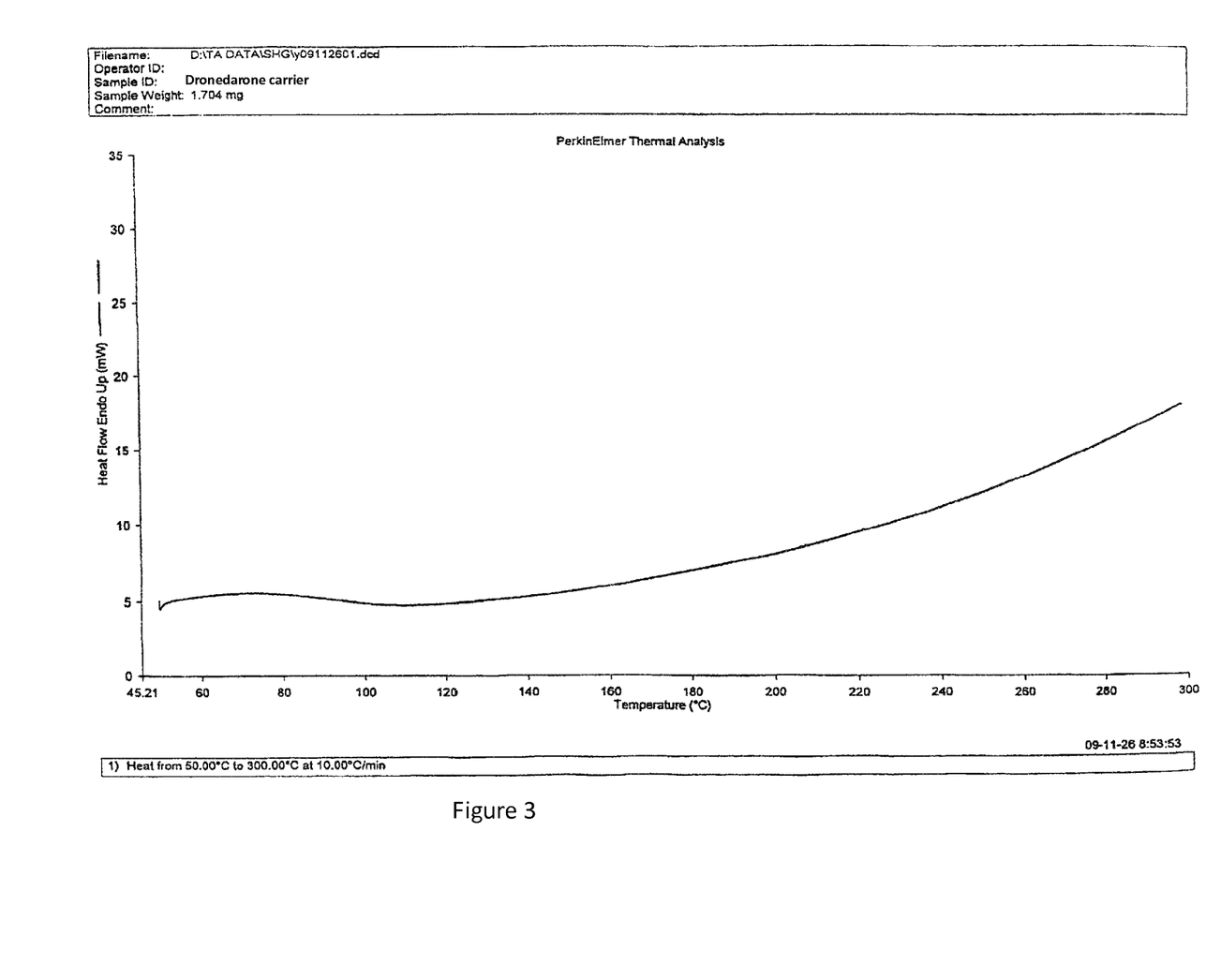
FIG. 3: the DSC spectrum of PVP-K30.
Figure 4:
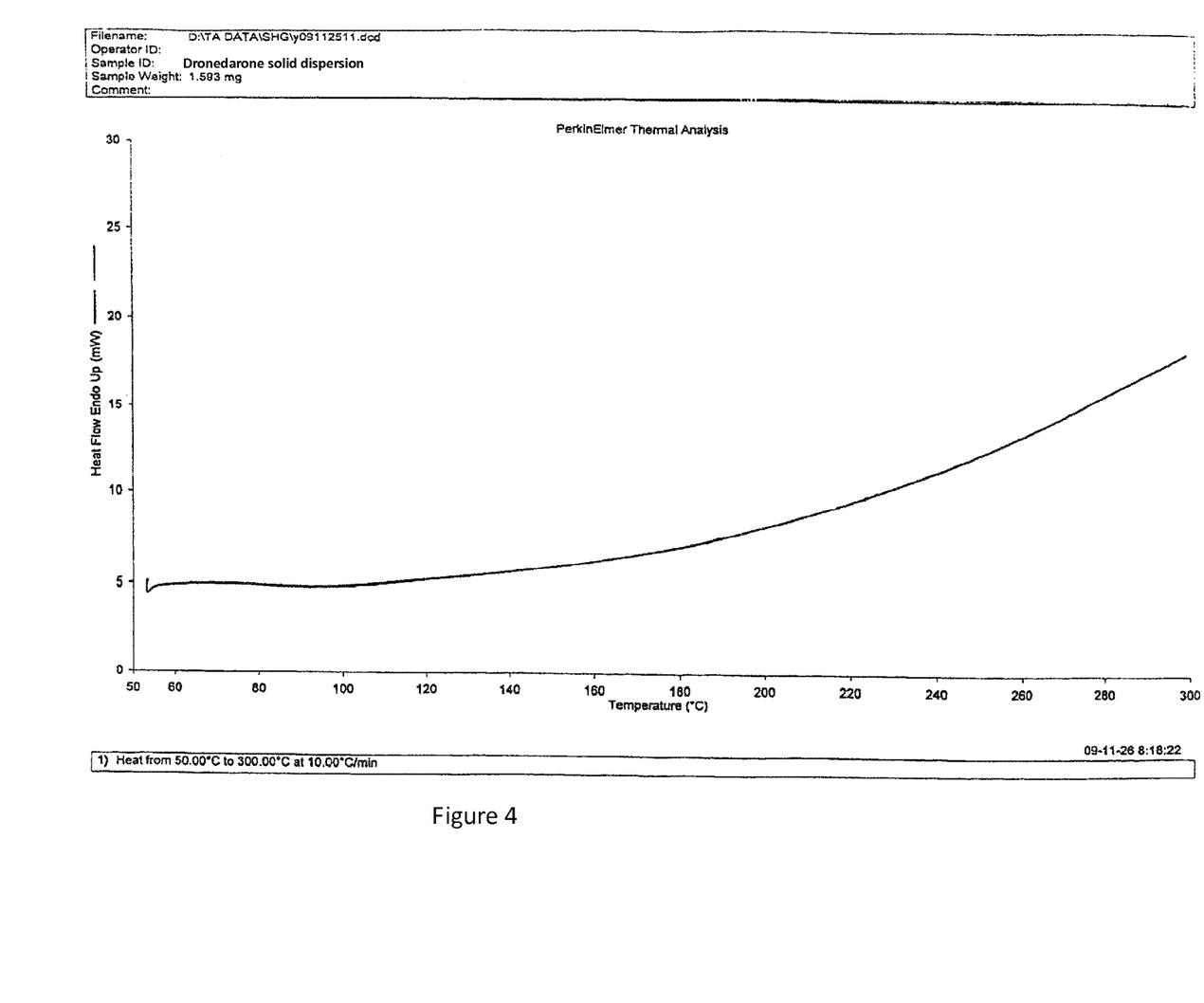
FIG. 4: the DSC spectrum of dronedarone hydrochloride in the solid dispersion obtained in Example 2.

FIG. 2 shows the DSC spectrum of dronedarone hydrochloride raw drug.
FIG. 3 shows the DSC spectrum of PVP carrier.
FIG. 4 shows the DSC spectrum of dronedarone hydrochloride in solid dispersion obtained in Example 2.

As shown in the figures above, crystalline endothermic peak of dronedarone hydrochloride raw drug appeared at about 144° C., indicating that the raw drug was present in the form of crystalline state. However, in the figure of the solid dispersion, the endothermic peak disappeared, indicating that the drug in the solid dispersion was converted to an amorphous or molecular state from crystalline state.

Test Example 3

Powder X-Ray Diffraction Tests (PXRD)

Working conditions: scan speed: 10 degrees/min; step: 0.02 degrees; target: Cu; pipe pressure/pipe flow: 40 kV/50 mA. The powder X-ray diffraction tests were conducted on the dronedarone hydrochloride raw drug, povidone PVP-K30 and the solid dispersion prepared in Example 2.

Figure 5:
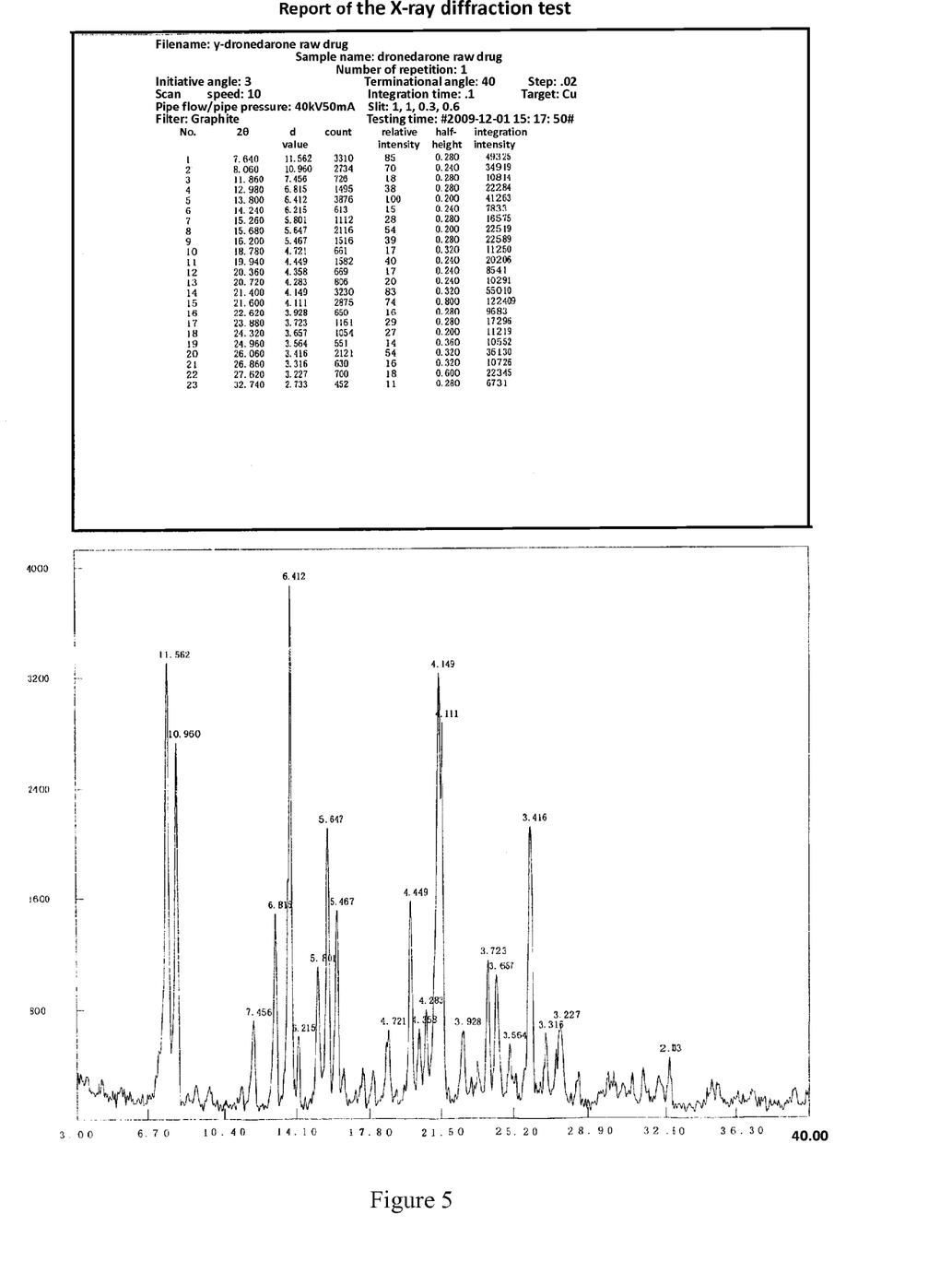
FIG. 5: the X-ray diffraction spectrum of dronedarone hydrochloride.

FIG. 5 shows the X-ray diffraction spectrum of dronedarone hydrochloride raw drug.

Figure 6:
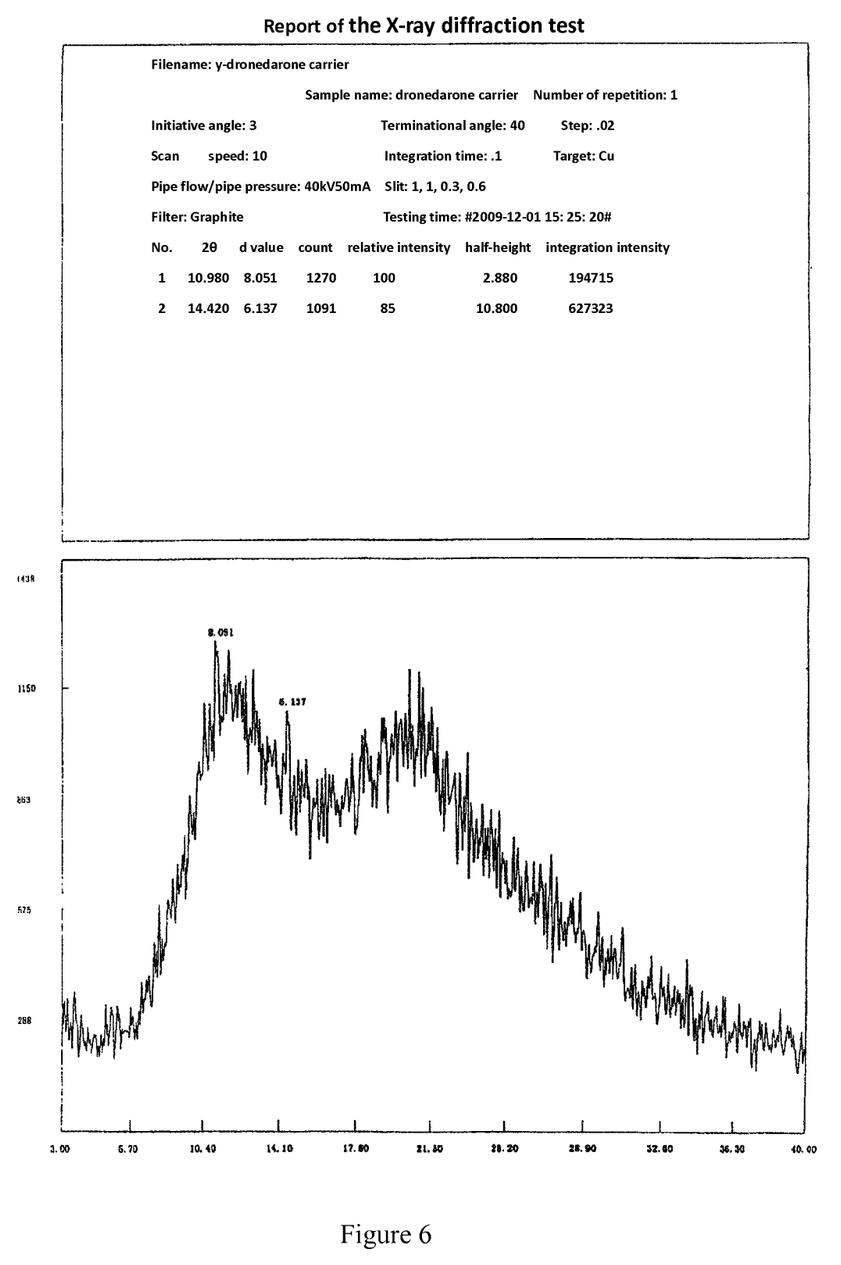
FIG. 6: the X-ray diffraction spectrum of PVP-K30.

FIG. 6 shows the X-ray diffraction spectrum of PVP carrier.

Figure 7:
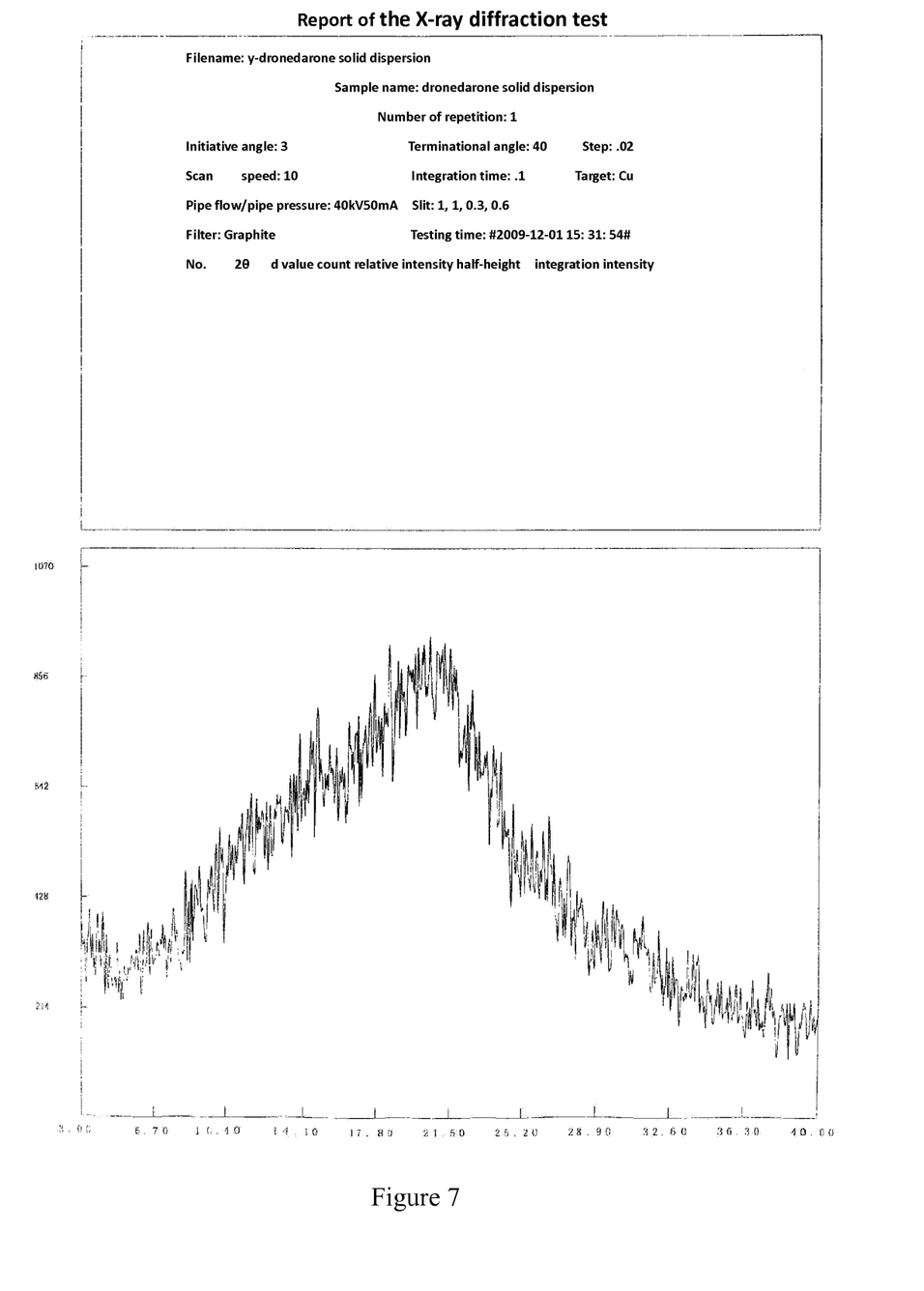
FIG. 7: the X-ray diffraction spectrum of dronedarone hydrochloride in the solid dispersion obtained in Example 2.

FIG. 7 shows the X-ray diffraction spectrum of dronedarone hydrochloride in the solid dispersion obtained in Example 2.

As shown in the figures above, apparent crystalline diffraction peaks of dronedarone hydrochloride raw drug appeared at 2θ=7.64, 8.06, 12.98, 13.80, 15.68, 21.40, 21.60, 26.06 etc.; weaker crystalline diffraction peaks of povidone PVP-K30 appeared at 2θ=10.98, 14.42. However, in the X-ray diffraction spectrum of the solid dispersion, all the crystalline diffraction peaks of the drug disappeared, which further confirmed that the drug was present in the solid dispersion in amorphous or molecular state.

What is claimed is:

1. A solid dispersion of dronedarone or a pharmaceutically acceptable salt thereof, wherein the solid dispersion consists of dronedarone or the pharmaceutically acceptable salt thereof serving as an active ingredient, and a carrier material, wherein the carrier material is selected from the group consisting of povidone, copovidone, hydroxypropyl cellulose, and a mixture thereof.

2. The solid dispersion of dronedarone according to claim 1, wherein the carrier material is selected from the group consisting of povidone K-b 17, povidone K-25, povidone K-30, povidone K-90 hypromellose E5, hypromellose E3, hypromellose E50 and hypromellose K-4M.

3. The solid dispersion of dronedarone according to claim 1, wherein the carrier material is selected from the group consisting of povidone K-17, povidone K-25, povidone K-30 and povidone K-90.

4. The solid dispersion of dronedarone according to claim 1, wherein the carrier material is povidone K-30.

5. The solid dispersion of dronedarone according to claim 1, wherein the weight ratio of dronedarone to the carrier material is 1:0.2-15.

6. The solid dispersion of dronedarone according to claim 1, wherein the dronedarone in the solid dispersion is amorphous.

7. The solid dispersion of dronedarone according to claim 1, wherein the pharmaceutically acceptable salt is selected from the group consisting of hydrochloride, citrate, maleate and tartrate salts.

8. A method for preparing the solid dispersion of dronedarone according to claim 1, wherein the method is selected from the group consisting of a hot melting extrusion method and a solvent method.

9. The method for preparing the solid dispersion of dronedarone according to claim 8, wherein the method is the solvent method, comprising:
dissolving dronedarone and the carrier material in a solvent; stirring until the mixture of dronedarone and the carrier material is dissolved and then removing the solvent to obtain a dry mass; and crushing the dry mass to obtain the solid dispersion.

10. The method for preparing the solid dispersion of dronedarone according to claim 9, wherein the solvent is one or more selected from the group consisting of dichloromethane, methanol, ethanol, acetone, chloroform and isopropanol.

11. The method for preparing the solid dispersion of dronedarone according to claim 9, wherein the solvent is an organic solvent.

12. The method for preparing the solid dispersion of dronedarone according to claim 10, wherein the weight ratio of the total weight of dronedarone and the carrier material to the organic solvent is 1:1.0-10.0.

13. The method for preparing the solid dispersion of dronedarone according to claim 10, wherein the organic solvent is removed by a method of drying under reduced pressure.

14. The solid dispersion of dronedarone according to claim 1, wherein the weight ratio of dronedarone to the carrier material is 1:0.5-10.

15. The solid dispersion of dronedarone according to claim 1, wherein the weight ratio of dronedarone to the carrier material is 1:1.0-7.5.

16. The solid dispersion of dronedarone according to claim 1, wherein the weight ratio of dronedarone to the carrier material is 1:1.5-5.0.

17. The solid dispersion of dronedarone according to claim 1, wherein the pharmaceutically acceptable salt is hydrochloride salt.

18. The method for preparing the solid dispersion of dronedarone according to claim 10, wherein the weight ratio of the total weight of dronedarone and the carrier material to the organic solvent is 1:1.0-5.0.

* * * * *